United States Patent [19]
Albert et al.

[11] Patent Number: 5,753,627
[45] Date of Patent: May 19, 1998

[54] USE OF CERTAIN COMPLEXED SOMATOSTATIN PEPTIDES FOR THE INVIVO IMAGING OF SOMATOSTATIN RECEPTOR-POSITIVE TUMORS AND METASTASIS

[75] Inventors: Rainer Albert, Basel, Switzerland; Eric P. Krenning, Capelle; Steven W. J. Lamberts, Rotterdam, both of Netherlands; Janos Pless, Basel, Switzerland

[73] Assignee: Novartis AG, Basel, Switzerland

[21] Appl. No.: 470,099

[22] Filed: Jun. 6, 1995

Related U.S. Application Data

[62] Division of Ser. No. 328,296, Oct. 24, 1994, abandoned, which is a continuation of Ser. No. 34,336, Mar. 22, 1993, abandoned, which is a continuation of Ser. No. 709,868, Jun. 3, 1991, abandoned, which is a continuation-in-part of Ser. No. 445,815, Dec. 4, 1989, abandoned.

[51] Int. Cl.$^6$ .............................. A61K 38/00; C07K 7/08; C07K 14/655; C07K 7/50
[52] U.S. Cl. .............................. 514/16; 514/11; 530/311; 530/317; 530/328; 530/304; 530/324
[58] Field of Search .............................. 530/311, 304, 530/324, 317, 328; 514/12, 11

[56] References Cited

U.S. PATENT DOCUMENTS 5,460,785  10/1995  Rhodes et al. .............................. 424/1.49

FOREIGN PATENT DOCUMENTS

| | | |
|---|---|---|
| 187622 | 7/1986 | European Pat. Off. . |
| 2199831 | 7/1988 | United Kingdom . |
| 2206352 | 1/1989 | United Kingdom . |

OTHER PUBLICATIONS

Kirk–Othmer Encyclopedia of Chemical Technology, 3rd Ed., vol. 5, pp. 339–341.

European Journal of Nuclear Medicine, vol. 20, No. 8, pp. 716–731 (1993).

Mallinckrodt Nuclear Medicine OctreoScan®.

Cell Biophysics, vol. 21, pp. 93–107 (1992).

Journal of Clinical Endocrinology and Metabolism, vol. 68, No. 2, pp. 239–246 (1989).

*Primary Examiner*—Cecilia J. Tsang
*Assistant Examiner*—S. G. Marshall
*Attorney, Agent, or Firm*—Joseph J. Borovian

[57] ABSTRACT

Somatostatin peptides bearing at least one chelating group for a detectable element, said chelating group being linked to an amino group of said peptide, and said amino group having no significant binding affinity for somatostatin receptors, in free or salt form, are complexed with a detectable element and are useful as a pharmaceutical, e.g. a radiopharmaceutical for in vivo imaging of somatostatin receptor positive tumors or for therapy.

11 Claims, No Drawings

USE OF CERTAIN COMPLEXED SOMATOSTATIN PEPTIDES FOR THE INVIVO IMAGING OF SOMATOSTATIN RECEPTOR-POSITIVE TUMORS AND METASTASIS

This is a division of application Ser. No. 08/328,296, filed Oct. 24, 1994, which in turn is a continuation of application Ser. No. 08/034,336, filed Mar. 22, 1993, which in turn is a continuation of application Ser. No. 07/709,868, filed Jun. 3, 1991, which in turn is a continuation-in-part of application Ser. No. 07/445,815, filed Dec. 4, 1989, all of which are now abandoned.

The invention relates to polypeptides, process for their production, pharmaceutical preparations containing them and their use as a pharmaceutical, e.g. for treatment of somatostatin receptor positive tumors or as in vivo diagnostic imaging agents.

In the last few years a high incidence of somatostatin receptors has been demonstrated in a variety of human tumors, e.g. pituitary tumors, central nervous system tumors, breast tumors, gastro-enteropancreatic tumors and their metastases. Some of them are small or slow-growing tumors which are difficult to precisely localize by conventional diagnosis methods.

In vitro visualization of somatostatin receptors has been performed through autoradiography of tumoral tissues using radio-iodinated somatostatin or somatostatin analogues, e.g. [$^{125}$I-Tyr$^{11}$] somatostatin-14 (Taylor, J. E. et al., Life Science (1988) 43: 421), or [$^{125}$I-Tyr$^3$] SMS 201–995 also called [$^{125}$I] 204–090 (Reubi, J. C. et al., Brain Res. (1987) 406: 891; Reubi, J. C. et al., J. Clin. Endocr. Metab. (1987) 65: 1127; Reubi, J. C. et al., Cancer Res. (1987) 47: 551; Reubi, J. C. et al., Cancer Res. (1987) 47: 5758; Reubi, J. C. Adv. in Biosciences (1988) 69: 193).

New somatostatin peptides useful in therapeutic and which can be labelled for in vivo diagnostic and therapeutic applications have now been found.

According to the invention, there is provided a somatostatin peptide bearing at least one chelating group for a detectable element, this chelating group being linked to an amino group of said peptide, and this amino group having no significant binding affinity for somatostatin receptors.

These compounds are referred to thereafter as LIGANDS OF THE INVENTION. They possess at least one chelating group capable of reacting with a detectable element, e.g. a radionuclide, a radio-opaque element or a paramagnetic ion, to form a complex and further are capable of binding to somatostatin receptors, e.g. expressed or overexpressed by tumors or metastases.

The chelating group is linked by a covalent bond to the amino group of the peptide.

The chelating group is preferably attached to the terminal amino group of the somatostatin peptide.

According to the invention, the chelating group may be attached either directly or indirectly, e.g. by means of a spacer or bridging group, to the amino group of the somatostatin peptide.

One group of LIGANDS is that wherein the chelating group is attached directly to the amino group of the somatostatin peptide.

Another group of LIGANDS is that wherein the chelating group is attached indirectly by a bridging or a spacer group to the amino group of the somatostatin peptide.

Preferably the chelating group is attached by an amide or thiourea bond to the peptide.

The term somatostatin peptides includes the naturally occurring somatostatin (tetradecapeptide) and its analogues or derivatives.

By derivatives or analogues as used herein is meant any straight-chain or cyclic polypeptide derived from that of the naturally occurring tetradecapeptide somatostatin wherein one or more amino acid units have been omitted and/or replaced by one or more other amino acid radical(s) and/or wherein one or more functional groups have been replaced by one or more other functional groups and/or one or more groups have been replaced by one or several other isosteric groups. In general, the term covers all modified derivatives of a biologically active peptide which exhibit a qualitatively similar effect to that of the unmodified somatostatin peptide, e.g. they bind to somatostatin receptors and decrease hormone secretion.

Cyclic, bridge cyclic and straight-chain somatostatin analogues are known compounds. Such compounds and their preparation are described e.g. in European Patent Specifications EP-A-1295; 29,579; 215,171; 203,031; 214, 872; 298,732; 277,419. The contents of all the above publications including the specific compounds are specifically incorporated herein by reference.

Preferred LIGANDS OF THE INVENTION are those derived from the following somatostatin analogues:

A. Analogues of formula I

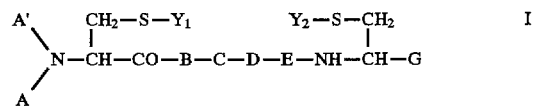

wherein

A is $C_{1-12}$alkyl, $C_{7-10}$phenylalkyl or a group of formula RCO—, whereby

RCO— is a) an L- or D-phenylalanine residue optionally ring-substituted by F, Cl, Br, NO$_2$, NH$_2$, OH, $C_{1-3}$alkyl and/or $C_{1-3}$alkoxy;

b) the residue of a natural or synthetic α-amino acid other than defined under a) above or of a corresponding D-amino acid, or c) a dipeptide residue in which the individual amino acid residues are the same or different and are selected from those defined under a) and/or b) above, the α-amino group of amino acid residues a) and b) and the terminal amino group of dipeptide residues c) being optionally mono-$C_{1-12}$alkylated, A' is hydrogen, $C_{1-12}$alkyl or $C_{7-10}$phenylalkyl, $Y_1$ and $Y_2$ represent together a direct bond or each of $Y_1$ and $Y_2$ is independently hydrogen or a radical of formulae (1) to (5)

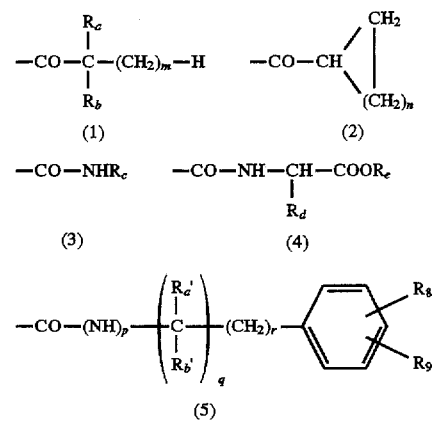

wherein $R_a$ is methyl or ethyl $R_b$ is hydrogen, methyl or ethyl m is a whole number from 1 to 4 n is a whole number from 1 to 5

$R_c$ is $(C_{1-6})$alkyl $R_d$ represents the substituent attached to the α-carbon atom of a natural or synthetic α-amino acid (including hydrogen)

$R_e$ is $(C_{1-5})$alkyl $R_a'$ and $R_b'$ are independently hydrogen, methyl or ethyl, $R_8$ and $R_9$ are independently hydrogen, halogen, $(C_{1-3})$alkyl or $(C_{1-3})$alkoxy, p is 0 or 17 q is 0 or 1, and r is 0, 1 or 2,

B is -Phe- optionally ring-substituted by halogen, $NO_2$, $NH_2$, OH, $C_{1-3}$alkyl and/or $C_{1-3}$alkoxy (including pentafluoroalanine), or β-naphthyl-Ala C is (L)-Trp- or (D)-Trp- optionally α-N-methylated and optionally benzene-ring-substituted by halogen, $NO_2$, $NH_2$, OH, $C_{1-3}$alkyl and/or $C_{1-3}$alkoxy, D is Lys, Lys in which the side chain contains O or S in β-position, γ-Lys or δ-Lys, optionally α-N-methylated, or a 4-aminocyclohexylAla or 4-aminocyclohexylGly residue E is Thr, Ser, Val, Phe, Ile or an aminoisobutyric or aminobutyric acid residue G is a group of formula

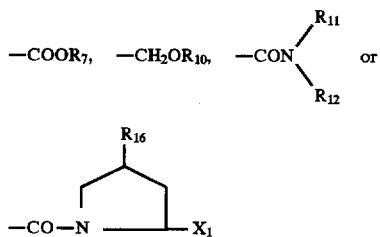

wherein $R_7$ is hydrogen or $C_{1-3}$alkyl, $R_{10}$ is hydrogen or the residue of a physiologically acceptable, physiologically hydrolysable ester, $R_{11}$ is hydrogen, $C_{1-3}$alkyl, phenyl or $C_{7-10}$phenyl-alkyl, $R_{12}$ is hydrogen, $C_{1-3}$alkyl or a group of formula —CH$(R_{1-3})$—$X_1$, $R_{13}$ is $CH_2OH$, —$(CH_2)_2$—OH, —$(CH_2)_3$—OH, or —$CH(CH_3)OH$ or represents the substituent attached to the α-carbon atom of a natural or synthetic α-amino acid (including hydrogen) and $X_1$ is a group of formula —$COOR_7$, —$CH_2OR_{10}$ or

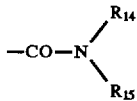

wherein $R_7$ and $R_{10}$ have the meanings given above, $R_{14}$ is hydrogen or $C_{1-3}$alkyl and $R_{15}$ is hydrogen, $C_{1-3}$alkyl, phenyl or $C_{7-10}$ phenylalkyl, and $R_{16}$ is hydrogen or hydroxy, with the proviso that when $R_{12}$ is —$CH(R_{13})$—$X_1$ then $R_{11}$ is hydrogen or methyl, wherein the residues B, D and E have the L-configuration, and the residues C and in the 2- and 7-position and any residues $Y_1$ 4) and $Y_2$ 4) each independently have the (L)- or (D)-configuration.

The significances of A and A' in formula I are preferably selected so that the compound contains a terminal —NH— group capable of being linked to a chelating agent.

In the compounds of formula I, the following significances are preferred either individually or in any combination or sub-combination:

1. A is $C_{7-10}$ phenylalkyl, especially phenethyl, or a group of formula RCO. Preferably A is a group of formula RCO.

1.1. When RCO has the meanings a), b) or c), the α-amino group of amino acid residues a) and b) and the terminal amino group of dipeptide residues c) is preferably non-alkylated or mono-$C_{1-12}$ alkylated, especially —$C_{1-8}$ alkylated, more especially -methylated. Most preferably the N-terminal is non-alkylated.

1.2. When RCO has the meaning a) this is preferably a') an L- or D-phenylalanine or -tyrosine residue optionally mono-N-$C_{1-12}$ alkylated. More preferably a') is an L- or D-phenylalanine residue.

1.3. When RCO has the meaning b) or c) the defined residue is preferably lipophilic. Preferred residues b) are thus b') α-amino acid residues having a hydrocarbon side chain, e.g. alkyl with 3, preferably 4, or more C atoms, e.g. up to 7 C-atoms, naphthylmethyl or heteroaryl, e.g. 3-(2- or 1-naphthyl)alanine, pyridylmethyl or tryptophane residue, said residues having the L- or D-configuration, and preferred residues c) are dipeptide residues in which the individual amino acid residues are the same or different and are selected from those defined under a') and b') above.

1.4. Most preferably RCO has the meaning a) especially the meaning a').

2. B is B', where B' is Phe or Tyr.

3. C is C', where C' is (D)Trp or Trp.

4. D is D', where D' is Lys, MeLys or Lys(ε-Me), especially Lys.

5. E is E', where E' is Val, Ser or Thr, especially Thr or Val.

6. G is G', where G' is a group of formula

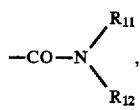

especially a group of formula

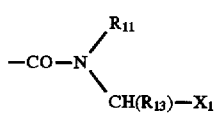

(in which case $R_{11}$=H or $CH_3$). In the latter case the moiety —$CH(R_{13})$—$X_1$ preferably has the L-configuration.

6.1. $R_{11}$ is preferably hydrogen.

6.2. As the substituent attached to the α-carbon atom of an amino acid (i.e. of formula $H_2N$—$CH(R_{13})$—COOH), $R_{13}$ is preferably —$CH_2OH$, —$CH(CH_3)$—OH, isobutyl, butyl, benzyl, naphthylmethyl, or 3-indolylmethyl or $R_{13}$ is —$(CH_2)_2$—OH or —$(CH_2)_3$—OH. It is especially —$CH_2OH$ or —$CH(CH_3)OH$.

6.3. $X_1$ is preferably a group of formula

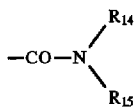

or —$CH_2$—$OR_{10}$, especially of formula —$CH_2$—$OR_{10}$ and $R_{10}$ is preferably hydrogen.

7. $Y_1$ and $Y_2$ represent together a direct bond or are each hydrogen.

The following individual compounds are illustrative of compounds of formula I:

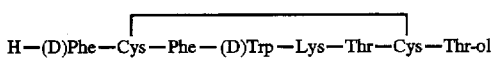

also known as octreotide

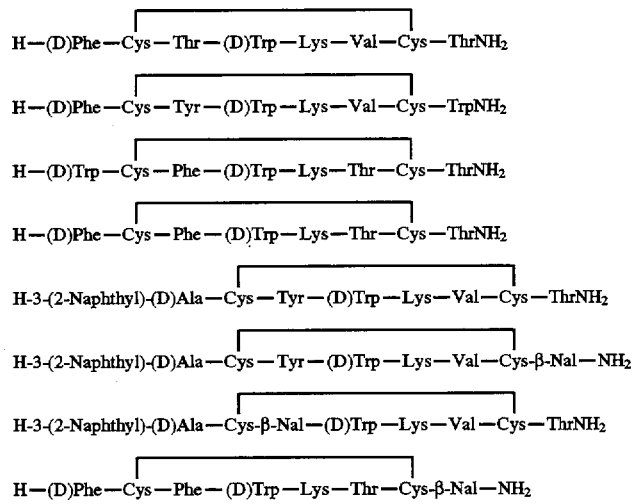

B. Analogues of formula II

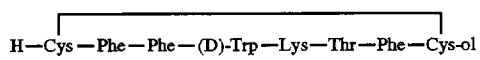    II

[see Vale et al., Metabolism, 27, Supp. 1, 139, (1978)]

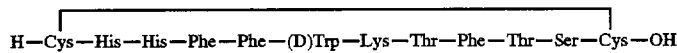    III (see EP-A-200, 188)

Particular preferred LIGANDS are those derived from

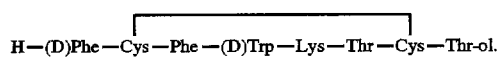

Suitable chelating groups are physiologically acceptable chelating groups capable of complexing a detectable element. According to one preferred embodiment, the chelating group has substantially a hydrophilic character. Examples of chelating groups include e.g. iminodicarboxylic groups, polyaminopolycarboxylic groups, e.g. those derived from non cyclic ligands e.g. ethylene diaminetetraacetic acid (EDTA), diethylene triamine pentaacetic acid (DTPA), ethylene glycol-O,O'-bis(2-aminoethyl)-N,N,N',N'-tetraacetic acid (EGTA), N,N'-bis(hydroxybenzyl)ethylenediami-ne-N, N'-diacetic acid (HBED) and triethylenetetramine hexaacetic acid (TTHA), those derived from macrocyclic ligands, e.g. 1,4,7,-10-tetra-azacyclododecane-N,N',N",N'"-tetraacetic acid (DOTA), 1,4,7,10-tetraazacyclotridecane-1, 4,7,10-tetraacetic acid (TITRA), 1,4,8,11-tetraazacyclotetradecane-N,N',N",N'"-tetra-acetic acid (TETA) and 1,4,8,11-tetraazacyclotetradecane (TETRA), those derived from substituted EDTA, DTPA, DOTA, TITRA or TETRA e.g. p-isothiocyanatobenzyl-EDTA, 1-(p-isothiocyanatobenzyl)-DTPA, 2-(p-isothiocyanatobenzyl)-DOTA, 12-(p-isothiocyanatobenzyl)-TITRA or 1-(p-isothiocyanatobenzyl)-TETRA, those derived from N-substituted or C-substituted macrocyclic amines including also cyclames, e.g. as disclosed in EP 304,780 A1 and in WO 89/01476-A, groups of formula IV or V

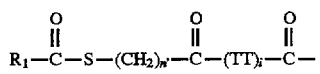   IV

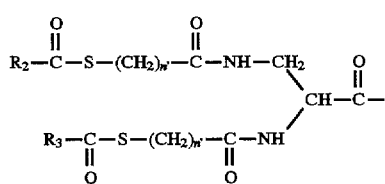   V wherein each of $R_1$, $R_2$ and $R_3$ independently is $C_{1-6}$alkyl, $C_{6-8}$aryl or $C_{7-9}$arylalkyl, each optionally substituted by OH, $C_{1-4}$alkoxy, COOH or $SO_3H$, n' is 1 or 2, i is an integer from 2 to 6, and TT are independently α or β amino acids linked to each other by amide bonds, groups derived from bis-aminothiol derivatives, e.g. compounds of formula VI

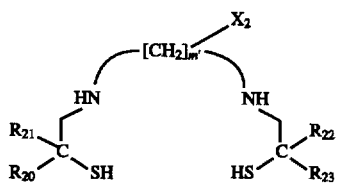     VI wherein each of $R_{20}$, $R_{21}$, $R_{22}$ and $R_{23}$ independently is hydrogen or $C_{1-4}$alkyl, $X_2$ is a group capable of reacting with the amino group of the peptide, and m' is 2 or 3, e.g. as disclosed in EP-A2-322,876, the contents of which being incorporated herein by reference groups derived from dithiasemicarbazone derivatives, e.g. compounds of formula VII

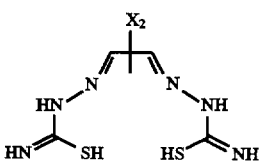     VII wherein $X_2$ is as defined above, groups derived from propylene amine oxime derivatives, e.g. compounds of formula VIII

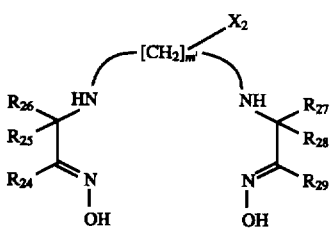     VIII wherein each of $R_{24}$, $R_{25}$, $R_{26}$, $R_{27}$, $R_{28}$ and $R_{29}$ independently are hydrogen or $C_{1-4}$alkyl, and $X_2$ and m' are as defined above, groups derived from diamide dimercaptides, e.g. compounds of formula IX

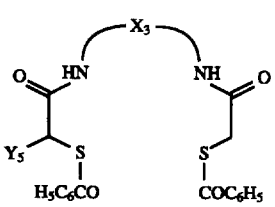     IX wherein $X_3$ is a divalent radical optionally substituted and bearing a group capable of reacting with the N-amino group of the peptide, e.g. $C_{1-4}$alkylene or phenylene bearing a group $X_2$, and $Y_5$ is hydrogen or $CO_2R_{30}$, wherein $R_{30}$ is $C_{1-4}$alkyl, or groups derived from porphyrins, e.g. N-benzyl-5,10, 15,20-tetrakis-(4-carboxyphenyl)porphine or TPP bearing a group $X_2$ as defined above, or from Deferoxamine (Desferal).

Aryl is preferably phenyl. Arylalkyl is preferably benzyl. Examples of $X_2$ include radicals of formula —$(X_4)_{n'}$—, —$X_5$ wherein $X_4$ is $C_{1-6}$alkylene; $C_{1-6}$alkylene optionally attached to the carbon atom by an oxygen atom or —NH—; or phenyl-$C_{1-3}$alkyl; n" is 0 or 1 and $X_5$ is —NCS, a carboxy group or a functional derivative thereof, e.g. acid halide, anhydride or hydrazide. When $X_4$ is phenyl-$C_{1-3}$alkyl, $X_5$ is preferably in para. A preferred significance for $X_2$ is e.g. p-isothiocyanatobenzyl. It is understood that $X_2$ is attached to one of the carbon atom of —[$CH_2$]$_{m'}$— or =CH—CH= in replacement of an hydrogen atom.

The chelating group may be attached either directly or indirectly to the N-amino group of the somatostatin peptide. When it is attached indirectly, it is preferably linked through a bridging or spacer group, for example a group of formula (α1)

$$Z—R_{35}—CO—$$ (α1)

$R_{35}$ is $C_{1-11}$alkylene, $C_{2-11}$alkenylene or —CH(R')— wherein R' is the residue attached in α to a natural or synthetic α-amino acid, e.g. hydrogen, $C_{1-11}$alkyl, aminobutyl, benzyl, optionally substituted benzyl, naphthyl-methyl, pyridyl-methyl, Z is a functional moiety capable of covalently reacting with the chelating agent.

Z may be for example a group which can form an ether, ester or amide bonding with the chelating group. Z is preferably CO or NH, more preferably NH.

Particularly preferred bridging or spacer groups are those derived from a dicarboxylicacid, e.g. succinyl, and those derived from an amino acid, e.g. β-Ala, Lys.

The chelating groups, when comprising carboxy, —$SO_3H$ and/or amino groups may exist in free form or in salt form.

Preferred chelating groups are those derived from polyamino-polycarboxylic groups, e.g. those derived from EDTA, DTPA, DOTA, TETA, TETRA, TITRA or 3,3,9,9-tetramethyl-4,8-diazaundecane-2,10-dione dioxime (HMPAO) or from such groups substituted, e.g. by a p-isothiocyanato-phenyl$C_{1-3}$alkyl, preferably p-isothiocyanatobenzyl. Chelating groups derived from DTPA are most preferred.

In the LIGANDS OF THE INVENTION the chelating group, when polyfunctional, may be linked either to a single somatostatin peptide molecule or to more than one somatostatin peptide molecules e.g. to two somatostatin peptide molecules.

Alternatively the LIGANDS OF THE INVENTION may contain more than one chelating groups, e.g. 2 chelating groups, preferably identical. Examples of such LIGANDS are compounds bearing a spacer with two reaction sites, e.g. a radical of formula (α1) wherein Z is NH and $R_{35}$ is aminobutyl.

The LIGANDS OF THE INVENTION may exist e.g. in free or salt form. Salts include acid addition salts with e.g. organic acids, polymeric acids or inorganic acids, for example hydrochlorides and acetates, and salt forms obtainable with the carboxylic or sulphonic acid groups present in the chelating group, e.g. alkali metal salts such as sodium or potassium, or substituted or unsubstituted ammonium salts.

The present invention also includes a process for the production of the LIGANDS OF THE INVENTION. They may be produced by analogy to known methods.

The LIGANDS OF THE INVENTION may be produced for example as follows:

a) removing at least one protecting group which is present in a somatostatin peptide bearing a chelating group, or b) linking together by an amide bond two peptide fragments each of them containing at least one amino acid or amino alcohol in protected or unprotected form and one of them containing the chelating group, wherein the amide bond is in such a way that the desired amino acid sequence is obtained, and stage a) of the process is then optionally effected, or c) linking together a chelating agent and the desired somatostatin peptide in protected or unprotected form in such a way that the chelating group is fixed on the desired N-amino group of the peptide, and stage a) is then optionally effected or, d) removing a functional group of an unprotected or a protected peptide bearing a chelating group or converting it into another functional group so that another unprotected or protected peptide bearing a chelating group is obtained and in the latter case stage a) of the process is effected, or e) oxidising a somatostatin peptide modified by a chelating group in which the mercapto groups of Cys radicals exist in free form so as to produce an analogue in which two Cys radicals are joined by an S-S-bridge and recovering the LIGAND thus obtained in free form or in salt form.

The above reactions may be effected in analogy with known methods, e.g. as described in the following examples, in particular processes a) and c). When the chelating group is attached by an amide bond or thiourea bond, this may be carried out analogously to the methods used for amide formation or reacting an isothiocyanate with an amine. Where desired, in these reactions, protecting groups which are suitable for use in peptides or for the desired chelating groups may be used for functional groups which do not participate in the reaction. The term protecting group may also include a polymer resin having functional groups.

When it is desired to attach the chelating group to the terminal amino group of a peptide or peptide fragment used as starting material, and which comprises one or more side chain amino groups, these side chain amino groups are conveniently protected with a protecting group, e.g. as used in peptide chemistry.

When it is desired to attach the chelating group to a side chain amino group of a peptide or peptide fragment used as starting material, and the peptide comprises a free terminal amino group, the latter is preferably protected with a protecting group.

The peptide fragment bearing the chelating group and used in stage b) may be prepared by reacting the peptide fragment comprising at least one amino acid or amino alcohol in protected or unprotected form with the chelating agent. The reaction may be performed in analogy with stage c).

The chelating groups of formula IV or V may be linked to a ting agent of formula IV' or V'

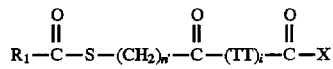

IV'

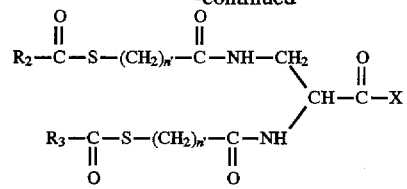

V' wherein X is an activating group capable of forming an amide bond with in the N-amino group of the peptide. The reaction may be performed as disclosed in EP 247,866 A1.

The chelating agent used in process step c) may be known or prepared in analogy with known procedures. The chelating agent is preferably such that it allows the introduction of the desired chelating group on the somatostatin peptide, e.g. a polyaminopolycarboxylic acid as disclosed, a salt, an anhydride or an azide thereof. The coupling of a polyamino polycarboxylic chelating agent via the anhydride may for example be carried out as disclosed by D. J. Hnatowich et al. in Int. J. Appl.Radiat. Isot., 33, 327–332 (1982). The coupling of a polyamino polycarboxylic chelating agent via the azide may be effected as disclosed in WO 91/01144.

Deferoxamine (or Desferal) is a known compound (cf. The Merck Index, Tenth Edition, 2839, 1983).

In the above process, when in the amino-acids, peptide fragments or peptides used as starting materials, the chelating group is attached through a bridging or spacer group to the peptide, e.g. a radical of formula ($\alpha_1$) as defined above, such amino-acids, peptide fragments or peptides may be prepared by reacting in conventional manner the corresponding amino-acids or peptides free of bridging or spacer group with a corresponding bridging or spacer-yielding compound, for example an acid or reactive acid derivative comprising the bridging or spacer group, e.g. an acid of formula Z—$R_{35}$—COOH or a reactive acid derivative thereof such as an active ester. Examples of active ester groups or carboxy activating groups are e.g. 4-nitrophenyl, pentachlorophenyl, pentafluorophenyl, succinimidyl or 1-hydroxy-benzotriazolyl.

Alternatively the chelating agent may first be reacted with a bridging or spacer group-yielding compound, in order to bear the bridging or spacer group and then be reacted in conventional manner with the peptide, peptide fragment or amino-acid.

The LIGANDS OF THE INVENTION may be purified in conventional manner, e.g. by chromatography. Preferably the LIGANDS OF THE INVENTION contain less than 5% by weight of peptides free of chelating groups.

According to a further embodiment, the LIGANDS OF THE INVENTION can be complexed with a detectable element.

Accordingly, the present invention also provides the LIGANDS OF THE INVENTION as defined above which are complexed with a detectable element (hereinafter referred to as CHELATES OF THE INVENTION), in free form or in salt form, their preparation and their use for in vivo diagnostic and therapeutic treatment.

By detectable element is meant any element, preferably a metal ion which exhibits a property detectable in therapeutic or in vivo diagnostic techniques, e.g. a metal ion which emits a detectable radiation or a metal ion which is capable of influencing NMR relaxation properties.

Suitable detectable metal ions include for example heavy elements or rare earth ions, e.g. as used in CAT scanning (Computer axial tomography), paramagnetic ions, e.g. $Gd^{3+}$, $Fe^{3+}$, $Mn^{2+}$ and $Cr^{2+}$, fluorescent metal ions, e.g. $Eu^{3+}$, and radionuclides, e.g. γ-emitting radionuclides, β-emitting radionuclides, α-emitting radionuclides, positron-emitting radionuclides e.g. $^{68}Ga$.

Suitable γ-emitting radionuclides include those which are useful in diagnostic techniques. The γ-emitting radionuclides advantageously have a half-life of from 1 hour to 40 days, preferably from 5 hours to 4 days, more preferably from 12 hours to 3 days. Examples are radionuclides derived from Gallium, Indium, Technetium, Ytterbium, Rhenium and Thallium e.g. $^{67}$Ga, $^{111}$In, $^{99m}$Tc, $^{169}$Yb, $^{90}$Y and $^{186}$Re. Preferably the γ-radionuclide is selected depending on the metabolism of the LIGAND OF THE INVENTION or somatostatin peptide used. More preferably the LIGAND OF THE INVENTION is chelated with a γ-radionuclide having a longer half-life than the half-life of the somatostatin peptide on the tumor.

Further radionuclides suitable for use in imaging are positron-emitting radionuclides, e.g. as mentioned above.

Suitable remitting radionuclides include those which are useful in therapeutic applications, for example $^{88}$Y, $^{90}$Y, $^{67}$Cu, $^{186}$Re, $^{188}$Re, $^{169}$Er, $^{121}$Sn, $^{127}$Te, $^{143}$Pr, $^{198}$Au, $^{109}$Pd, $^{165}$Dy, $^{32}$P, $^{142}$Pr. The β-radionuclide advantageously have a half-life of from 2.3 hrs to 14.3 d, preferably from 2.3 to 100 hrs. Preferably the β-emitting radionuclide is selected in order to have a longer half-life than the half-life of the somatostatin peptide on the tumor.

Suitable α-emitting radionuclides are those which are used in therapeutic treatments, e.g. $^{211}$At, $^{212}$Bi.

The CHELATES OF THE INVENTION may be prepared by reacting the LIGAND with a corresponding detectable element yielding compound, e.g. a metal salt, preferably a water-soluble salt. The reaction may be carried out by analogy with known methods, e.g. as disclosed in Perrin, Organic Ligand, Chemical Data Series 22. NY Pergamon Press (1982); in Krejcarit and Tucker, Biophys. Biochem. Res. Com. 77: 581 (1977) and in Wagner and Welch, J. Nucl. Med. 20: 428 (1979).

Preferably the complexing of the LIGAND is effected at a pH at which the LIGAND OF THE INVENTION is physiologically stable.

Alternatively the detectable element may also be provided to the solution as a complex with an intermediate chelating agent, e.g. a chelating agent which forms a chelate complex that renders the element soluble at the physiological pH of the LIGAND but is less thermodynamically stable than the CHELATE. Example of such an intermediate chelating agent is 4,5-dihydroxy-1,3-benzene-di-sulfonic acid (Tiron). In such a process, the detectable element exchanges the ligand.

The CHELATES OF THE INVENTION may also be produced by linking together a chelating agent complexed with the detectable element, and a somatostatin peptide in protected or unprotected form and if desired removing at least one protecting group which is present. The same reaction may be performed with a chelating agent complexed with a non detectable metal ion and then in the resulting complexed peptide the metal ion may be replaced by the desired detectable element.

The CHELATES OF THE INVENTION may also be produced by linking together a chelating agent complexed with the detectable element, and a somatostatin peptide fragment comprising at least one amino acid in protected or unprotected form and then continuing the peptide synthesis step by step until the final peptide sequence is obtained and if desired removing at least one protecting group which is present. Instead of the detectable element the chelating agent may be complexed with a non detectable metal and this metal may then be replaced by the detectable element in the resulting complexed somatostatin peptide.

Where the chelating group is attached through a bridging or spacer group to the somatostatin peptide, e.g. through a radical of formula ($\alpha_1$) as defined above, either the somatostatin peptide or peptide fragment or the chelating agent may bear said bridging or spacer group.

The above mentioned reactions may be effected in analogy to known methods. Depending on the chelating group present, the labeling efficiency may approach 100% so that purification is not required. Radionuclides such as for example Technetium-99m may be used in oxidized form, e.g. Tc-99m pertechnetate, which may be complexed under reducing conditions.

The above mentioned reactions are conveniently effected under conditions avoiding trace metal contamination. Preferably distilled de-ionized water, ultrapure reagents, chelation-grade radioactivity etc. are used to reduce the effects of trace metal.

The CHELATES OF THE INVENTION may exist e.g. in free or salt form. Salts include acid addition salts with e.g. organic acids, polymeric acids or inorganic acids, for example hydrochlorides and acetates, and salt forms obtainable with the carboxylic acid groups present in the molecule which do not participate to the chelate formation, e.g. alkali metal salts such as sodium or potassium, or substituted or unsubstituted ammonium salts.

The CHELATES OF THE INVENTION and their pharmaceutical acceptable salts exhibit pharmaceutical activity and are therefore useful either as an imaging agent, e.g. visualisation of somatostatin receptor positive tumors and metastases when complexed with a paramagnetic, a γ-emitting metal ion or a positron-emitting radionuclide, or as a radiopharmaceutical for the treatment in vivo of somatostatin receptor positive tumors and metastases when complexed with a α- or β-radionuclide, as indicated by standard tests.

In particular, the CHELATES OF THE INVENTION possess affinity for somatostatin receptors expressed or overexpressed by tumors and metastases, as indicated in standard in vitro binding assays.

A somatostatin receptor positive tumor originating from the human gastro intestinal tract is removed from a patient and immediately put on ice and within a maximal delay of 30 min frozen at −80° C. For further autoradiography this frozen material is cut on a cryostat (Leitz 1720) in 10 μm sections, mounted on precleaned microscope slides and stored at −20° C. for at least 3 days to improve adhesion of the tissue to the slide. The sections are preincubated in Tris-HCl buffer (50 mM, pH 7.4), containing CaCl$_2$ (2 mM) and KCl (5 mM), for 10 min at ambient temperature and then washed twice for 2 min in the same buffer without additional salts added. The sections are then incubated with a CHELATE OF THE INVENTION for 2 hours at ambient temperature in Tris-HCl buffer (170 mM, pH 7.4), containing bovine serum albumin (10 g/l), bacitracin (40 mg/l) and MgCl$_2$ (5 mM) to inhibit endogenous proteases. Non-specific binding is determined by adding

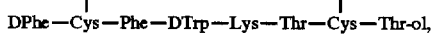

DPhe—Cys—Phe—DTrp—Lys—Thr—Cys—Thr-ol, at a concentration of 1 μM. Incubated sections are washed twice for 5 min in cold incubation buffer containing 0.25 g/l BSA. After a brief dip in distilled water to remove excess salts, the sections are dried quickly and apposed to [$^3$H]-LKB films. After a time exposure of about 1 week in X-ray cassettes, it is observed that the CHELATES OF THE INVENTION, e.g. a radionuclide CHELATE, give very good results in labeling the tumoral tissue without labeling the surrounding healthy tissue when added at a concentration of about $10^{-10}$ to $10^{-3}$M.

In this binding in vitro assay, it is observed that the compound of Example 5 labels the somatostatin receptor positive tumoral tissue with high specificity and low non-specific background.

The affinity of the CHELATES OF THE INVENTION for somatostatin receptors can also be shown by in vivo testing.

Rats bearing transplantable exocrine pancreatic somatostatin receptor positive tumors are treated with an intravenous injection of a CHELATE OF THE INVENTION. Injection site is the penis vein. Immediately after administration, the animals are positioned on the collimator of a gamma-camera and the distribution of radioactivity is monitored at various time intervals.

Biodistribution of radioactivity may also be determined through serial sacrifice of a number of such treated rats and determination of the organ radioactivity.

After administration of a CHELATE OF THE INVENTION, e.g. a radionuclide CHELATE, for example a γ-emitting CHELATE, at a dosage of from 1 to 5 μg/kg of LIGAND labeled with 0.1 to 2 mCi radionuclide the tumor site becomes detectable together with the organs where excretion essentially takes place. Compound of Example 5 is administered i.v. to the animals at a dosage corresponding to 4 μg/kg body weight of compound of Example 1 labeled with 0.5 mCi $^{111}$In and the radioactivity is assessed 3 min, 10 min, 15 min, 20 min, 20 hrs and 48 hrs. 3 minutes after injection, radioactivity is detected in the kidneys, urinary bladder and in the tumor site. Radioactivity is increasing and is very intensely localized on the tumor site 20 hrs after injection.

Accordingly, in a series of specific or alternative embodiments, the present invention also provides:

1. A method for in vivo detection of somatostatin receptor positive tumors or metastases in a subject which comprises a) administering a CHELATE OF THE INVENTION to said subject and b) recording the localisation of the receptors targeted by said CHELATE.

CHELATES OF THE INVENTION for use in the in vivo detection method of the invention are the CHELATES which are complexed with a γ-emitting radionuclide, a positron-emitting radionuclide or a paramagnetic metal ion, e.g. as indicated above.

The CHELATES OF THE INVENTION for use as an imaging agent in method (1) may be administered parenterally, preferably intravenously, e.g. in the form of injectable solutions or suspensions, preferably in a single injection. An appropriate dosage will of course vary depending upon, for exemple, the LIGAND and the type of detectable element used, e.g. the radionuclide. A suitable dose to be injected is in the range to enable imaging by photoscanning procedures known in the art. When a radiolabeled CHELATE OF THE INVENTION is used, it may advantageously be administered in a dose having a radioactivity of from 0.1 to 50 mCi, preferably 0.1 to 30 mCi, more preferably 0.1 to 20 mCi.

In animals an indicated dosage range may be of from 0.1 to 10 μg/kg of LIGAND labeled with 0.1 to 2 mCi γ-emitting radionuclide e.g. $^{111}$In. In larger mammals, for example humans, an indicated dosage range may be of from 1 to 200 μg LIGAND labeled with 0.1 to 50 mCi, preferably 0.1 to 30 mCi, e.g. 3 to 15 mCi, γ-emitting radionuclide, depending on the γ-emitting radionuclide used. For example with In, it is preferred to use a radioactivity in the lower range, whereas with Tc, it is preferred to use a radioactivity in the upper range.

The enrichment in the tumorigenic sites with the CHELATES may be followed by the corresponding imaging techniques, e.g. using nuclear medicine imaging instrumentation, for example a scanner, γ-camera , rotating γ-camera, each preferably computer assisted; PET-scanner (Positron emission tomography); MRI equipment or CAT scanning equipment.

The CHELATES OF THE INVENTION, e.g. a major part of the γ-emitting CHELATES is substantially excreted through the kidneys and does not significantly accumulate in the liver.

2. A method for in vivo treatment of somatostatin receptor positive tumors and metastases in a subject in need of such a treatment which comprises administering to said subject a therapeutically effective amount of a CHELATE OF THE INVENTION.

CHELATES OF THE INVENTION for use in the in vivo treatment method of the invention are the CHELATES complexed with a α- or β-emitting radionuclide as defined above.

Dosages employed in practising the therapeutic method of the present invention will of course vary depending e.g. on the particular condition to be treated, for example the volume of the tumor, the particular CHELATE employed, for example the half-life of the CHELATE in the tumor, and the therapy desired. In general, the dose is calculated on the basis of radioactivity distribution to each organ and on observed target uptake. For example the CHELATE may be administered at a daily dosage range having a radioactivity of from 0.1 to 3 mCi/kg body weight, e.g. 1 to 3 mCi, preferably 1 to 2 mCi/kg body weight.

In animals an indicated dosage range may be of from 0.1 to 5 μg/kg of LIGAND labeled with 0.1 to 3 mCi α- or β-emitting radionuclide, e.g. $^{90}$Y. In larger mammals, for example humans, an indicated daily dosage range is of from 1 to 200 μg LIGAND labeled with 0.1 to 3 mCi/kg body weight, e.g. 0.1 to 2 mCi/kg body weight α- or β-emitting radionuclide, conveniently administered in divided doses up to 4 times a day.

The α- or β-emitting CHELATES OF THE INVENTION may be administered by any conventional route, in particular parenterally, e.g. in the form of injectable solutions or suspensions. They may also be administered advantageously by infusion, e.g. an infusion of 30 to 60 min. Depending on the site of the tumor, they may be administered as close as possible to the tumor site, e.g. by means of a catheter. The mode of administration selected may depend on the dissociation rate of the CHELATE used and the excretion rate.

The CHELATES OF THE INVENTION may be administered in free form or in pharmaceutically acceptable form. Such salts may be prepared in conventional manner and exhibit the same order of activity as the free compounds.

The CHELATES OF THE INVENTION for use in the method of the present invention may preferably be prepared shortly before the administration to a subject, i.e. the radiolabeling with the desired detectable metal ion, particularly the desired α-, β- or γ-radionuclide, may be performed shortly before the administration.

The CHELATES OF THE INVENTION may be suitable for imaging or treating tumors such as pituitary, gastroenteropancreatic, central nervous system, breast, prostatic, ovarian or colonic tumors, small cell lung cancer, paragangliomas, neuroblastomas, pheochromocytomas, medullary thyroid carcinomas, myelomas, etc. and metastases thereof.

According to a further embodiment of the invention, the γ-emitting CHELATES OF THE INVENTION may also be used as imaging agent for the evaluation of the kidney function.

Groups of five mice are used. Each mouse is injected intravenously through a tail vein with 0.1 ml containing 1 mCi of a CHELATE OF THE INVENTION. The mice are then placed in metabolic cages for the collection of excreted urine. At 10 or 120 min. post-injection, the urethras are ligated and the mice anesthetized with chloroform. Imaging of the uropoietic system is carried out using the usual imaging technique. In this test, the γ-emitting CHELATES OF THE INVENTION improves imaging of renal excretion when administered at a dosage of from 0.1 to 30 mCi.

Accordingly, the present invention also provides a method for in vivo evaluation of the kidney function in a subject which comprises administering to said subject an effective amount of a γ-emitting CHELATE and recording the kidney function.

According to a further aspect of the invention, there is provided:

i. a pharmaceutical composition comprising a LIGAND OF THE INVENTION in free or in pharmaceutically acceptable salt form, together with one or more pharmaceutically acceptable carriers or diluents therefor;

ii. a pharmaceutical composition comprising a CHELATE according to the invention in free or in pharmaceutically acceptable salt form, together with one or more pharmaceutically acceptable carriers or diluents therefor.

Such compositions may be manufactured in conventional manner.

A composition according to the invention may also be presented in separate package with instructions for mixing the LIGAND with the metal ion and for the administration of the resulting CHELATE. It may also be presented in twin-pack form, that is, as a single package containing separate unit dosages of the LIGAND and the detectable metal ion with instructions for mixing them and for administration of the CHELATE. A diluent or carrier may be present in the unit dosage forms.

In the following examples, all temperatures are in °C. and $[\alpha]_D^{20}$-values uncorrected. The following abbreviations are employed:

Boc tert.-butoxycarbonyl
TFA trifluoroacetic acid
AcOH acetic acid
DMF dimethyl formamide
Fmoc 9-fluorenylmethoxycarbonyl
DOTA 1,4,7,10-tetra-azacyclododecane-1,4,7,10-tetraacetic acid
DTPA diethylene triamine pentaacetic acid
HMPAO 3,3,9,9-tetramethyl-4,8-diazaundecane-2,10-dione-dioxime
TITRA 1,4,7,10-tetraazacyclotridecane-1,4,7,10-tetraacetic acid
TETRA 1,4,8,11-tetraazacyclotetradecane

EXAMPLE 1

DTPA—DPhe—Cys—Phe—DTrp—Lys—Thr—Cys—Thr-ol 1.1 g of

DPhe—Cys—Phe—DTrp—Lys(ε-Boc)—Thr—Cys—Thr-ol in free base (1 mM), are dissolved in 5 l of dioxan/H₂O 1/1 (v/v) and reacted with 5 g NaHCO₃. The 520 mg of DTPA dianhydride is slowly added with stirring. The reaction mixture is stirred for a further 30 min and dry-frozen. The residue is dissolved in 250 ml water and the pH is adjusted to pH 2.5 with concentrated HCl. The precipitated product is filtered out, washed and dried over phosphorus pentoxide. After chromatography on a silica-gel column, the following products are isolated: 230 mg of DTPA—DPhe—Cys—Phe—DTrp—Lys(ε-Boc)—Thr—Cys—Thr-ol and 500 mg of the corresponding dimer DTPA⟨DPhe—Cys—Phe—DTrp—Lys(ε-Boc)⟩Thr—Cys—Thr-ol)₂.

3 ml of TFA are mixed with 200 mg of

DTPA—DPhe—Cys—Phe—DTrp—Lys(ε-Boc)—Thr—Cys—Thr-ol.

After 5 min at room temperature, the mixture is precipitated with diisopropylether, filtered out and dried. The residue is desalted over Duolite and lyophilised to yield 150 mg of the title compound:

$[\alpha]_D^{20}$=−26,6°(c=1 95% AcOH).

The starting material may be produced as follows:

a) H—DPhe—Cys—Phe—DTrp—Lys(Boc)—Thr—Cys—Thr-ol 2.25 g of di-tert.butyl-pyrocarbonate, dissolved in 30 ml of DMF, are slowly added in drops at room temperature to a solution of 10 g of H—DPhe—Cys—Phe—DTrp—Lys—Thr—Cys—Thr-olacetate in 100 ml of DMF. After two hours at room temperature, the solvent is drawn off under vacuum, and 200 ml of diisopropylether are added to the residue. The deposit which is being formed is filtered off, washed with diisopropylether and dried. The crude product is purified by chromatography over silica gel (eluant: CH₂Cl₂/MeOH 9/1) and is then isolated as a white amorphous powder.

$[\alpha]_D^{20}$=29.8°(c=1.28 in DMF).

EXAMPLE 2

DTPA—(DPhe—Cys—Phe—DTrp—Lys—Thr—Cys—Thr-ol)₂

The fraction containing the intermediate product

DTPA—DPhe—Cys—Phe—DTrp—Lys(ε-Boc)—Thr—Cys—Thr-ol)₂ as obtained in example 1 is treated as described above for the corresponding monomeric form, the Boc protecting groups being removed to yield the title compound:

$[\alpha]_D^{20}$=−24,5°(c=0,55 95% AcOH).

EXAMPLE 3

H₂N—(CH₂)₅—CO—DPhe—Cys—Phe—DTrp—Lys—Thr—Cys—Thr-ol 0.56 g of

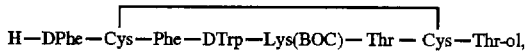

0.5 mmole of Fmoc-ε-aminocaproic acid and 115 mg of hydroxy-benzotriazole are dissolved in 10 ml of DMF and cooled to −30° C. To this solution is added a solution of 115 mg of dicyclohexylcarbodiimide in 5 ml of DMF (cooled to 10° C.).

After a reaction time of 24 hours, during which the mixture warms to the room temperature, the resulting dicyclohexylurea is filtered off and the filtrate is diluted with water to ten times its volume. The precipitated reaction product is filtered off, washed and dried over phosphorus pentoxide. The crude product is used without further purification for the next step.

b. Fmoc-cleavage 0.5 g of crude product from coupling reaction (a) are treated for 10 minutes at room temperature with 5 ml of DMF/piperidine 4/1 v/v (clear solution) and subsequently mixed with 100 ml of diisopropylether. The reaction product which is thus precipitated is filtered off, washed and dried. This crude product is used without further purification in the next step.

c. BOC cleavage 300 mg of crude product obtained in (1.b) are treated for 5 minutes at room temperature with 5 ml of 100% TFA (completely dissolved) and subsequently mixed with 50 ml of diisopropylether. After addition of 2 ml of HCl/diethylether, the resulting deposit is filtered off, washed and dried in a high vacuum. The end product is purified by chromatography on silica gel (CHCl$_3$/MeOH/H$_2$O/AcOH 7/3/0.5/0.5), with subsequent de-salting over Duolite (gradient: H$_2$O/AcOH 95/5)—H$_2$O/dioxane/AcOH 45/50/5). The title compound is obtained as an acetate (white lyophilisate).

$[\alpha]_D^{20}$=−32°(c=0.5 95% ACOH).

The resulting compound may be used for reaction with DTPA in accordance with the procedure of Examples 1 and 2.

EXAMPLE 4

By following the procedure disclosed in Examples 1 and 3, the following LIGAND can be prepared:

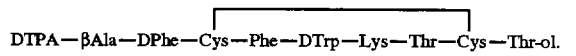

$[\alpha]_D^{20}$=−14,8°(c=0.5 95 % AcOH).

EXAMPLE 5

$^{111}$In labeled

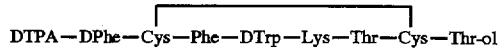

1 mg

is dissolved in 5 ml 0.01M acetic acid. The resulting solution is passed through a 0.22μ Millex-GV filter and dispensed in 0.1 ml portions and stored at −20° C. $^{111}$InCl$_3$ (Amersham, 1 mCi/100 μl) is prediluted in an equal volume of 0.5M sodium acetate and labeling is carried out by mixing the ligand with the InCl$_3$ solution and gentle homogenisation at room temperature.

HEPES buffer, pH 7.4, is then added to make a solution $10^{-6}$M.

EXAMPLE 6

$^{90}$Y labeled

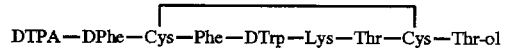

$^{90}$Y is obtained from a $^{90}$Sr-$^{90}$Y radionuclide generator. The construction of the generator, its elution and the conversion of the [$^{90}$Y]EDTA to the acetate complex are performed in accordance with the method disclosed by M. Chinol and D. J. Hnatowich in J. Nucl. Med. 28, 1465–1470 (1987). 1 mg of

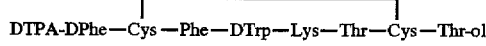

dissolved in 5 ml 0.01M acetic acid is allowed to warm to room temperature and 1.0 mCi of $^{90}$Y in 50 μl sterile 0.5M acetate is added. The mixture is then left undisturbed for 30 min to 1 hr to maximize chelation.

EXAMPLE 7

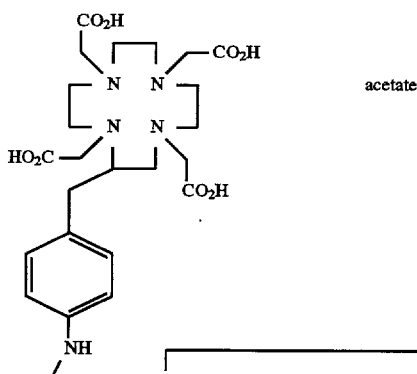

acetate

To a solution of 220 mg

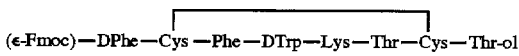

in 20 ml acetonitrile/water (3/1 v/v) and 0.14 ml triethylamine there is added 110 mg 2-(p-isothiocyanatobenzyl)-DOTA.

After a reaction time of 9 hours at room temperature the solution is diluted with water and freeze dried. The residue is purified by silica gel chromatography and then treated for 10 minutes with 10 ml piperidine/DMF (1/4 v/v). After removal of the solvent and the base, the raw compound is purified by chromatography on silica gel and desalted by RP-HPLC chromatography using a water/acetonitrile/acetic acid buffer system. The resulting title compound is lyophilized.

FAB-MS: 1570.9

2-(p-isothicyanatobenzyl)-DOTA, used as starting material, as well as 1-(p-isothiocyanatobenzyl)-DTPA, 12-(p-isothiocyanatobenzyl)-TITRA and 1-(p-isothiocyanatobenzyl)-TETRA used as starting material in the following Examples 8, 10 and 11, respectively, may be prepared e.g. as disclosed by M. W. Brechbiel and al. in Inorg. Chem., 25, 2772–2781 (1986) or Min K. Moi and C. F. Meares in J. Am.Chem. Soc., 110, 6266–6267 (1988).

The title compound is then labeled with $^{90}$Y according to the procedure of Example 6.

EXAMPLE 8

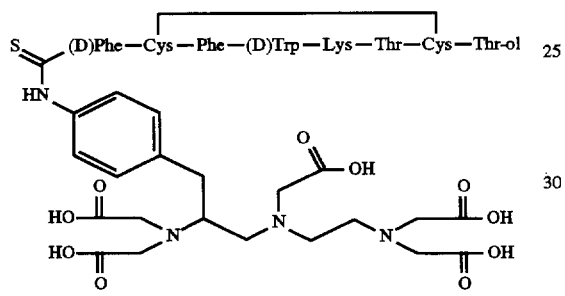

By repeating the procedure of Example 7 but using 1-(p-isothio-cyanatobenzyl)-DTPA instead of 2-(p-isothiocyanatobenzyl)-DOTA, the title compound is obtained.

FAB-MS: 1573.8 $[\alpha]_D^{20}$=−10.0°(c=0.12 in 95% AcOH)

The title compound is then labeled with $^{111}$In or $^{90}$Y according to the procedure of Example 5 or 6 respectively.

EXAMPLE 9

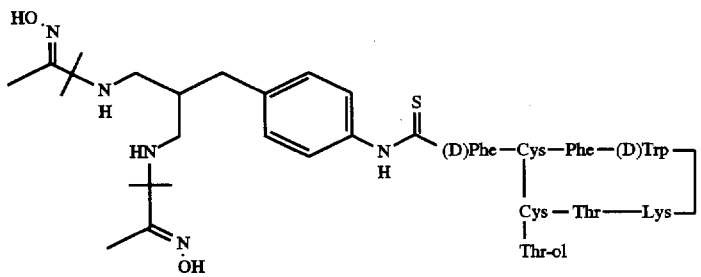

By repeating the procedure of Example 7 but using 6-(p-isothiocya-natobenzyl)-HMPAO instead of 2-(p-isothiocyanatobenzyl)-DOTA, the title compound is obtained.

FAB-MS: 1458.8

6-(p-isothiocyanatobenzyl)-HMPAO used as chelating agent may be prepared from 6-(p-nitrobenzyl)-HMPAO which is reduced to 6-(p-aminobenzyl)-HMPAO as follows:

15 ml methanol and 15 ml water are mixed and adjusted to pH 11 with 0.1N NaOH. 25 mg catalyst based on Pd/alox are added and after clearing of with hydrogen, prehydrogenation is performed. After 15 min. when a constant hydrogen level is reached, a solution of 0.25 g 6-(p-nitrobenzyl)-HMPAO in 15 ml 1:1 methanol/water is added and the mixture is stirred overnight. The resulting mixture is then filtered on Hyflo Super Cel, concentrated and dried under vacuo.

The resulting 6-(p-aminobenzyl)-HMPAO is then reacted with phosgen as disclosed by M. W. Brechbiel et al in Inorg. Chem. 25, 2772–2781, 1986.

6-(p-nitro-benzyl)-HMPAO may be prepared as disclosed by Parker et al. in Tetrahedron 45, No. 1, 21 (1989) and Meares et al. in Anal. Biochem., 142, 68 (1984).

The title compound is suitable for labeling with $^{99}$Tc.

EXAMPLE 10

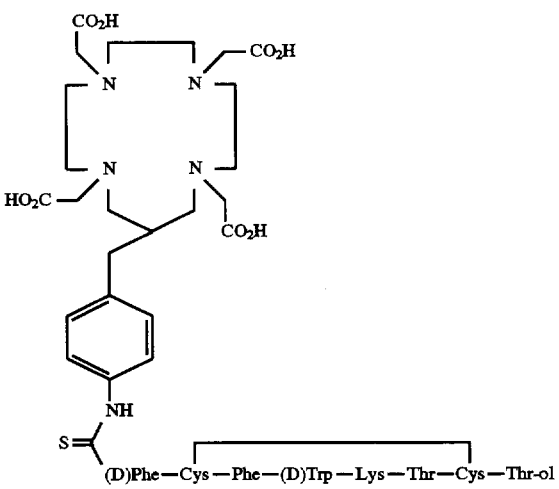

By repeating the procedure of Example 7 but using 12-(p-isothiocyanatobenzyl)-TITRA instead of 2-(p-isothiocyanatobenzyl)-DOTA, the title compound is obtained.

FAB-MS: 1584.9

EXAMPLE 11

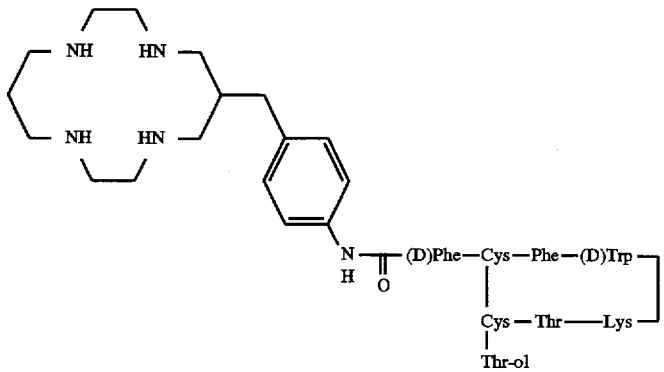

By repeating the procedure of Example 7 but using 1-(p-isothiocyanatobenzyl)-1,4,8,11-tetraazacyclotetradecane instead of 2-(p-isothiocyanatobenzyl)-DOTA, the title compound is obtained.

FAB-MS: 1366.8

The title compound is then labeled with $^{90}$Y according to the procedure of Example 6.

EXAMPLE 12

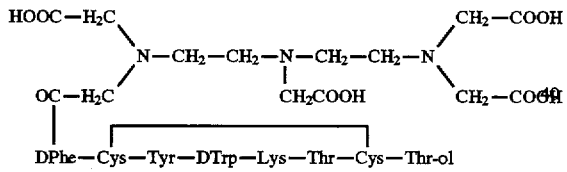

1.2 g of

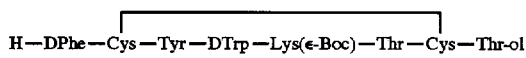

in free base (1 mM), are dissolved in 5 l of dioxan/H$_2$O 1/1 (v/v) and reacted with 5 g NaHCO$_3$. 520 mg DTPA dianhydride is slowly added with stirring. The reaction mixture is stirred for a further 30 min and dry-frozen. The residue is dissolved in 250 ml water and the pH is adjusted to pH 2.5 with concentrated HCl. The precipitated product is filtered out, washed and dried over phosphorus pentoxide. After cleavage of the Boc group by treatment with TFA, chromatography on a silica-gel column and desalting on a Duolite resin, the title compound is obtained.

$[\alpha]_D^{20}$=-6.4°(c=0.25 in 95% AcOH)

The title compound is then labeled with $^{111}$In according to the procedure of Example 5.

EXAMPLE 13

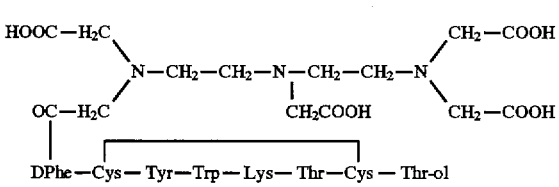

By repeating the procedure of Example 12 but using

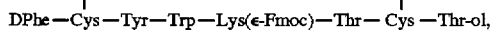

the title compound is obtained.

$[\alpha]_D^{20}$=-3.4°(c=0.25 in 95% AcOH)

The title compound is then labeled with $^{111}$In according to the procedure of Example 5.

EXAMPLE 14

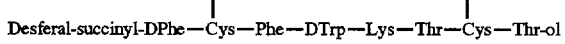

200 mg (0.164 mM)

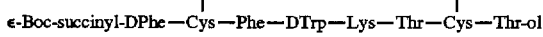

in solution in 20 ml DMF are cooled to -15°. There is added subsequently: 101 mg (0.18 mM) Desferal in base free form, 45 mg (0.33 mM) 1-hydroxybenzotriazole and 51.5 mg (0.25 mM) dicyclohexylcarbodiimide. The reaction mixture is warmed to room temperature and left for 18 hours at room temperature. After evaporation of the solvent under high vacuo, the residue is chromatographied on 50 g silica gel using a 8:2.0.125:0.125 mixture of chloroform/methanol/glacial acetic acid/water as eluent. The fractions containing the title compound are applied on 50 ml Duolite, washed salt free with water and eluted with a dioxan/water/1% acetic acid gradient. The resulting title compound is lyophilized.

MS =MH$^+$ 1661 $[\alpha]_D^{20}$=-7.4°(c=0.25 in 95% AcOH)

The compound used as starting material may be prepared as follows:

224 g (0.2 mM)

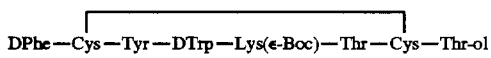
DPhe—Cys—Tyr—DTrp—Lys(ε-Boc)—Thr—Cys—Thr-ol are dissolved in 6 ml dioxan/water 1/1 and the solution is cooled to 4°. There is added 0.1 ml (0.58 mM) N-ethyldiisopropylamine and 24 mg (0.24 mM) succinic acid anhydride. After 1 hour the solution is lyophilized. The residue is treated with 10 ml methylene chloride, filtered and dried. The resulting product can be used tel quel for the reaction with Desferal.

EXAMPLE 15

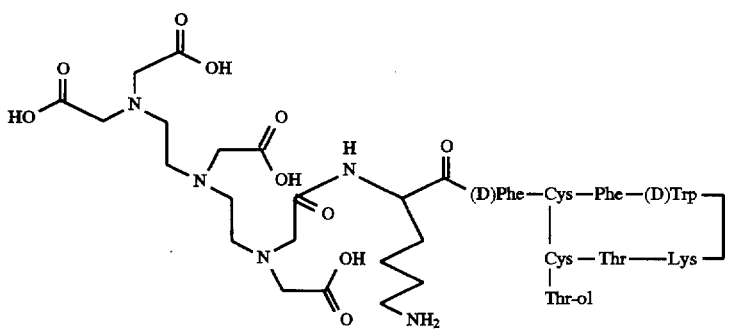

By repeating the procedure of Example 12 but using

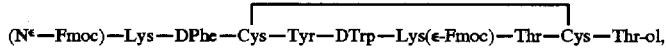
(N$^\alpha$—Fmoc)—Lys—DPhe—Cys—Tyr—DTrp—Lys(ε-Fmoc)—Thr—Cys—Thr-ol, the title compound is obtained.

The title compound may also be prepared as follows:
250 mg of the above mentioned protected peptide is dissolved in 5 ml DMF, and cooled to 40° C. To the solution there is added 0.131 ml N-ethyldiisopropylamin and 6.5 ml (0.183 mM) DTPA-azide. After 2 to 5 hrs at room temperature, the Fmoc protecting groups are removed with 1 ml piperidin. After 15 min. the mixture is evaporated, chromatographied on silica gel using a 7:5:2:2 chloroform/methanol/acetic acid/water mixture as eluent and evaporated. The residue is put on 50 g Duolite, washed salt free with water and rinsed with a 50/49/1 dioxane/water/acetic acid, yielding the title compound.

FAB-MS: 1522.8 [α]$_D^{20}$=−18.8°(c=0.6 in 95% AcOH)

DTPA-azide may be prepared as disclosed in WO 91/01144.

EXAMPLE 16

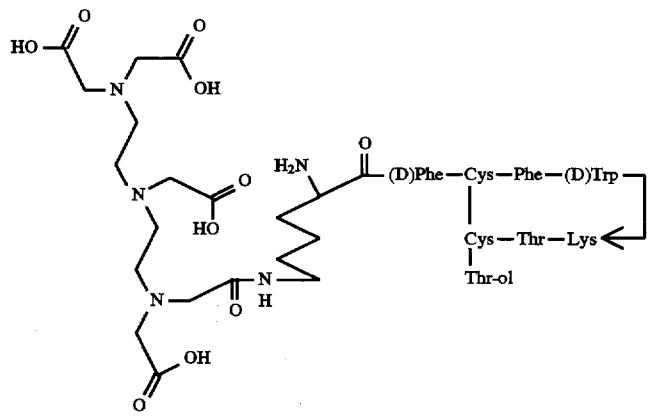

By repeating the procedure of Example 15 but using (Nα—Fmoc, Nε—Boc)—Lys—DPhe—Cys—Phe—DTrp—Lys(Fmoc)—Thr—Cys—Thr-ol, the title compound is obtained.

FAB-MS: 1522.8 $[\alpha]_D^{20} = -29°$ (c=0.31 in 95% AcOH)

EXAMPLE 17

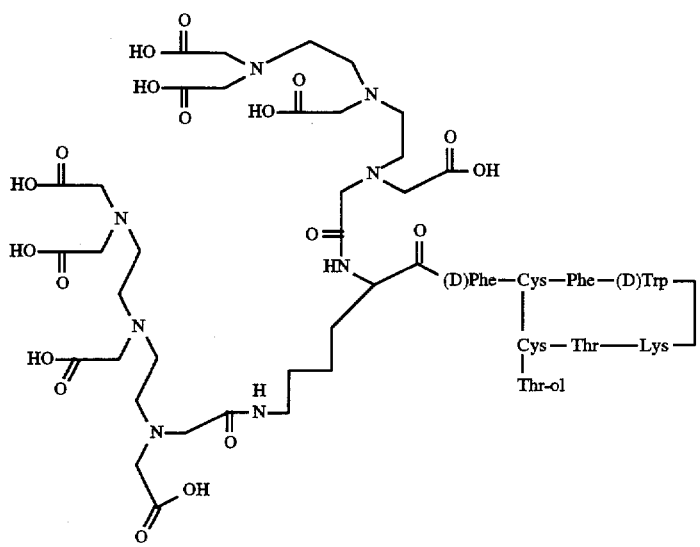

By repeating the procedure of Example 15 but using (Nα—Boc, Nε—Boc)—Lys—DPhe—Cys—Phe—DTrp—Lys(Fmoc)—Thr—Cys—Thr-ol, the title compound is obtained.

FAB-MS: 1898.1 $[\alpha]_D^{20} = -18.5°$ (c=0.3 in 95% AcOH)

EXAMPLE 18

68Ga labeled Desferal-succinyl-DPhe—Cys—Phe—DTrp—Lys—Thr—Cys—Thr-ol

A 68Ga generator based on tin oxide is eluted with 10 ml 5 mM Na₂EDTA at pH 7-8 at a flow rate of 1 ml/min. The resulting eluate is added to 15 ml 10M HCl and 25 ml diethyl ether. After mixing the phases the aqueous layer is rejected. The ether layer is further washed with 3×8 ml 6M HCl. The ether layer is reduced to dryness and redissolved in 300 µl ammonium acetate buffer (pH 4.5–5.0).

This 68Ga solution is added to 2 µg of the compound of Example 8 and the solution is vortexed for 20 seconds. There is added ca. 15µl 1M NaCl to render the solution isotonic prior to injection.

What is claimed is:

1. A method for in vivo detection of somatostatin receptor positive tumors and metastases in a subject comprising: a) administering to said subject a somatostatin peptide having a physiologically acceptable chelating group covalently linked directly or indirectly to the N-terminal amino group of the somatostatin peptide, which peptide is complexed by said chelating group with a detectable element selected from the group consisting of a γ-emitting radionuclide, a positron-emitting radionuclide, a fluorescent metal ion and a paramagnetic ion, and is in free base of pharmaceutically acceptable salt form, and b) recording the localization of the receptors targeted by said somatostatin peptide.

2. A method according to claim 1 wherein the somatostatin peptide has a chelating group covalently linked indirectly to the N-terminal amino group of said peptide through a spacer or bridging group.

3. A method according to claim 1 wherein the somatostatin peptide has a chelating group covalently linked to the N-terminal amino group of said peptide by an amide bond.

4. A method according to claim 1 wherein the somatostatin peptide has a chelating group covalently linked to the N-terminal amino group of said peptide by a thiourea bond.

5. A method according to claim 1 wherein the somatostatin peptide is a compound of formula I

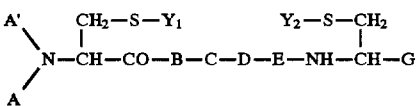

wherein

A is a group of formula RCO—,
where RCO— is a) an L- or D-phenylalanine residue optionally ring-substituted by F, Cl, Br, NO₂, NH₂, OH, C₁₋₃alkyl and/or C₁₋₃alkoxy;

b) the residue of a natural or a synthetic α-amino acid other than defined under a) above or of a corresponding D-amino acid, or c) a dipeptide residue in which the individual amino acid residues are the same or different and are selected from those defined under a) and/or b) above, the α-amino group of amino acid residues a) and b) and the N-terminal amino group of dipeptide residues c) being optionally mono-C₁₋₁₂alkylated, A' is hydrogen, C₁₋₁₂alkyl or C₇₋₁₀phenylalkyl, Y₁ and Y₂ represent together a direct bond or each of Y₁ and Y₂ is hydrogen, B is -Phe- optionally ring-substituted by halogen, NO₂, NH₂, OH, C₁₋₃alkyl and/or C₁₋₃alkoxy; or β-naphthyl-Ala, C is L-Trp- or D-Trp- optionally α-N-methylated and optionally benzene-ring-substituted by halogen, NO₂, NH₂, OH, C₁₋₃alkyl and/or C₁₋₃alkoxy, D is Lys, or a 4-aminocyclohexylAla or 4-aminocyclohexylGly residue, E is Thr, Ser, Val, Phe, Ile or an aminoisobutyric or aminobutyric acid residue, G is a group of formula

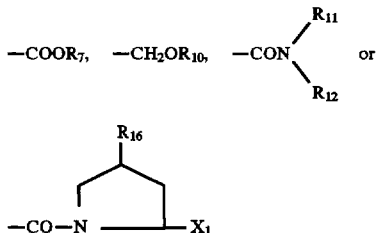

wherein

R₇ is hydrogen or C₁₋₃alkyl,

R₁₀ is hydrogen or the residue of a pharmaceutically acceptable, physiologically hydrolyzable ester, R₁₁ is hydrogen, C₁₋₃alkyl, phenyl or C₇₋₁₀phenylalkyl, R₁₂ is hydrogen, C₁₋₃alkyl or —CH(R₁₃)—X₁, R₁₃ is —CH₂ₒₕ, ₋₍cₕ₂₎₂—OH, —(CH₂)₃—OH, or —CH(CH₃) OH or represents the substituent attached to the α-carbon atom of a natural or a synthetic α-amino acid and X₁ is a group of formula —COOR₇, —CH₂ ₒᵣ₁₀ or —CONR₁₄R₅, wherein R₇ and R₁₀ have the meanings given above, R₁₄ is hydrogen or C₁₋₃alkyl, R₁₅ is hydrogen, C₁₋₃alkyl, phenyl or C₇₋₁₀phenylalkyl, and R₁₆ is hydrogen or hydroxy, with the proviso that when R₁₂ is —CH(R₁₃)—X₁, then R₁₁ is hydrogen or methyl, wherein the residues B, D and E have the L-configuration, and the residues C and G in the 2- and 7-position independently have the (L)- or (D)- configuration, in free base or pharmaceutically acceptable salt form.

6. A method according to claim 5 wherein the chelating group is selected from the group consisting of iminodicarboxylic groups, polyaminopolycarboxylic groups, groups derived from macrocyclic amines, groups of formula IV or V

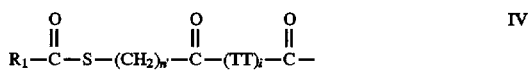

wherein each of

R₁, R₂ and R₃ independently is C₁₋₆alkyl, C₆₋₈aryl or C₇₋₉arylalkyl, each optionally substituted by OH, C₁₋₄alkoxy, COOH or SO₃H, n' is 1 or 2, i is an integer from 2 to 6, and TT are independently α or β amino acids linked to each other by amide bonds, groups derived from bis-aminothiol derivatives, groups derived from dithiasemicarbazone derivatives, groups derived from propylene amine oxime derivatives, groups derived from diamide dimercaptides, groups derived from porphyrins and groups derived from Deferoxamine.

7. A method according to claim 5 wherein the chelating group is derived from ethylene diaminetetraacetic acid (EDTA), diethylene triamine pentaacetic acid (DTPA), ethylene glycol-O,O'-bis(2-aminoethyl)-N,N,N',N'-tetraacetic acid (EGTA), N,N'-bis(hydroxybenzyl)ethylenediamine-N, N'-diacetic acid (H BED), triethylenetetramine hexaacetic acid (TTHA), substituted EDTA or -DTPA, 1,4,7,10-tetraazacyclododecane-N,N',N'',N'''-tetraacetic acid (DOTA) or 1,4,8,11-tetraazacyclotetradecane-N,N',N'',N'''-tetraacetic acid (TETA).

8. A method according to claim 5 wherein the chelating group is derived from ethylene diaminetetraacetic acid (EDTA), diethylene triamine pentaacetic acid (DTPA), 1,4,7,10-tetraazacyclododecane-N,N',N'',N'''-tetraacetic acid (DOTA), 1,4,8,11-tetraazacyclotetradecane-N,N',N'',N'''-tetraacetic acid (TETA), 1,4,7,10-tetraazacyclotridecane-1,4,7,10-tetraacetic acid (TITRA), 1,4,8,11-tetraazacyclotetradecane (TETRA), 3,3,9,9-tetramethyl-4,8-diazaundecane-2,10-dione dioxime (HMPAO), or EDTA, DTPA, DOTA, TETA, TITRA, TETRA or HMPAO substituted by p-isothiocyanatophenyl C₁₋₃alkyl.

9. A method according to claim 5 wherein the peptide is

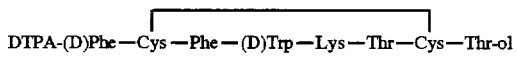

complexed with a detectable element, in free base or pharmaceutically acceptable salt form.

10. A method according to claim 9 wherein the peptide is complexed by the chelating group with a γ-emitting radionuclide or a positron-emitting radionuclide.

11. A method according to claim 10 wherein the peptide is complexed by the chelating group with $^{111}$In or $^{90}$Y.

* * * * *